United States Patent [19]
Byland et al.

[11] Patent Number: 5,456,698
[45] Date of Patent: Oct. 10, 1995

[54] PACEMAKER

[75] Inventors: James K. Byland, St. Paul; Michael D. DeFranco, Andover; William J. Hooper, Lake Elmo; James M. Sikorski, Moundsview; David L. Thompson, Fridley, all of Minn.

[73] Assignee: Medtronic, Inc., Minneapolis, Minn.

[21] Appl. No.: 158,832

[22] Filed: Nov. 23, 1993

Related U.S. Application Data

[63] Continuation of Ser. No. 766,602, Sep. 26, 1991, abandoned.

[51] Int. Cl.⁶ .................................................. A61N 1/375
[52] U.S. Cl. ............................................................ 607/36
[58] Field of Search ........................................ 607/36, 37

[56] References Cited

U.S. PATENT DOCUMENTS

| | | | |
|---|---|---|---|
| 3,053,356 | 9/1962 | Weinmann | 189/36 |
| 3,888,260 | 6/1975 | Fischell | 128/419 PS |
| 4,057,068 | 11/1977 | Comben | 607/36 |
| 4,243,042 | 1/1981 | Ware | 128/419 P |
| 4,314,562 | 2/1982 | Ware | 128/419 |
| 4,399,819 | 8/1983 | Cowdery | 128/419 P |
| 4,428,378 | 1/1984 | Anderson | 128/419 |
| 4,441,498 | 4/1984 | Nordling | 128/419 P |
| 4,735,205 | 4/1988 | Chachques et al. | |
| 4,759,463 | 7/1988 | Mazoin | 220/359 |
| 4,785,827 | 11/1988 | Fischer | 607/36 |
| 5,103,818 | 4/1992 | Maston et al. | 128/419 P |

Primary Examiner—William E. Kamm
Assistant Examiner—Scott M. Getzow
Attorney, Agent, or Firm—Reed A. Duthler; Harold R. Patton

[57] ABSTRACT

An enclosure for use in pacemaker as well as other implantable medical devices has a substantially planar lid which is welded to a circumferential flange formed on a deep drawn shield. The shield and lid form a "container" which is encased in a compliant shroud which isolates the welded flange from direct body contact and which enhances the biocompatibility of the entire device. A resilient and compliant shroud material accepts connector module components, integrates seals, provides storage for lead wrap, and provides a simple low cost and reliable method of attaching stimulating leads or other structures required by the medical device.

19 Claims, 11 Drawing Sheets

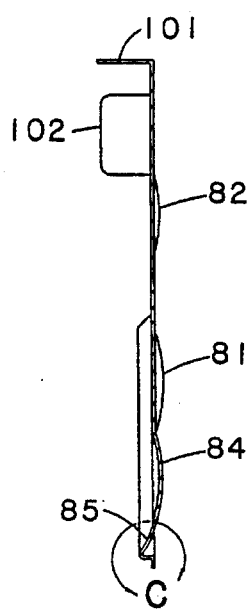
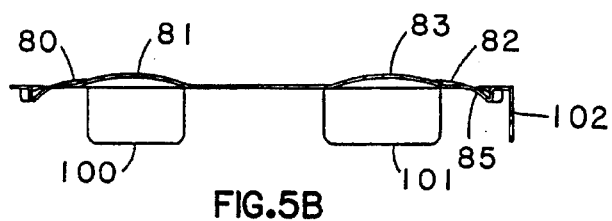
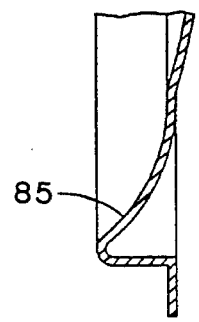
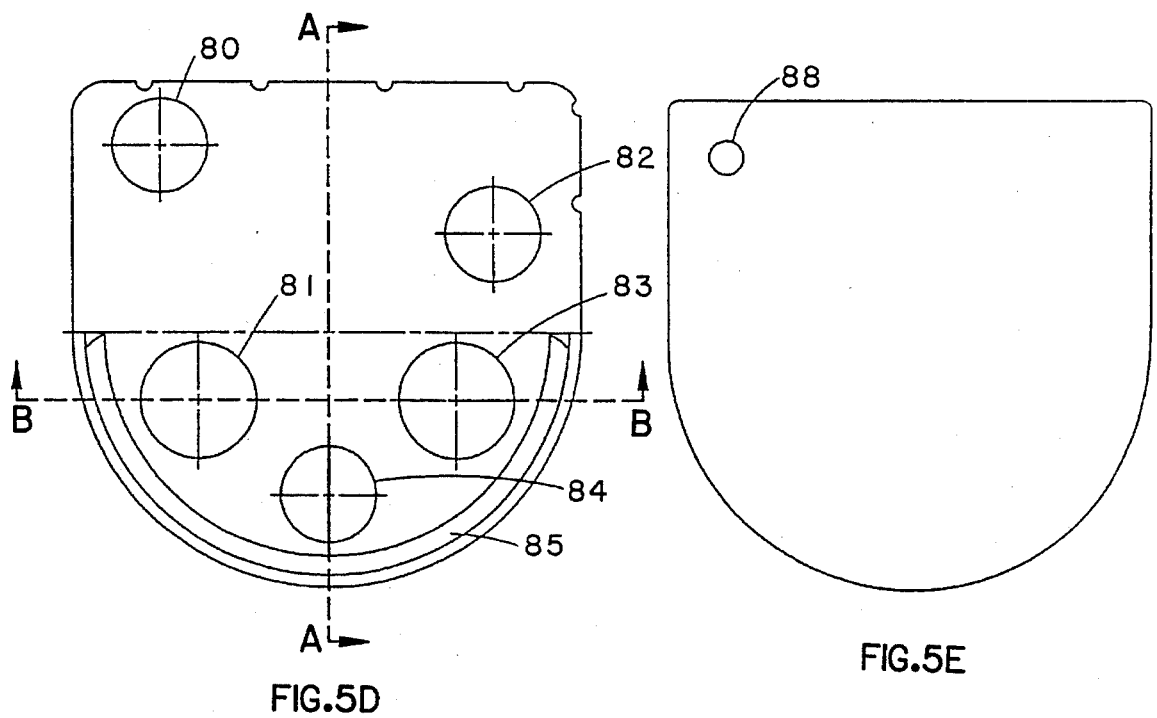
FIG.5A  FIG.5B  FIG.5C  FIG.5D  FIG.5E  FIG.5F

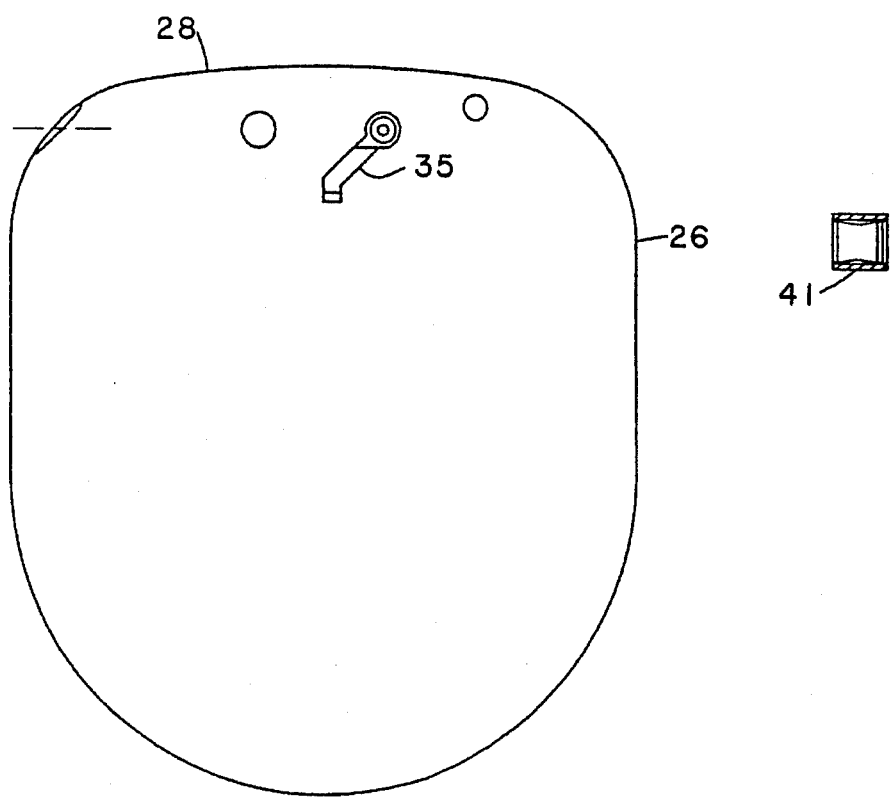
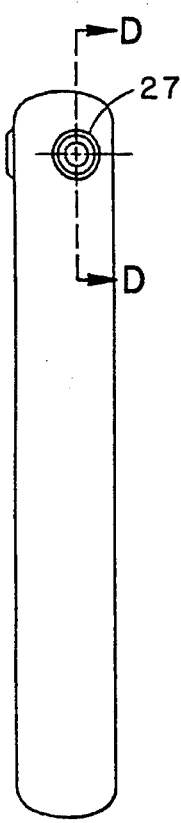
FIG.6A
FIG.6B
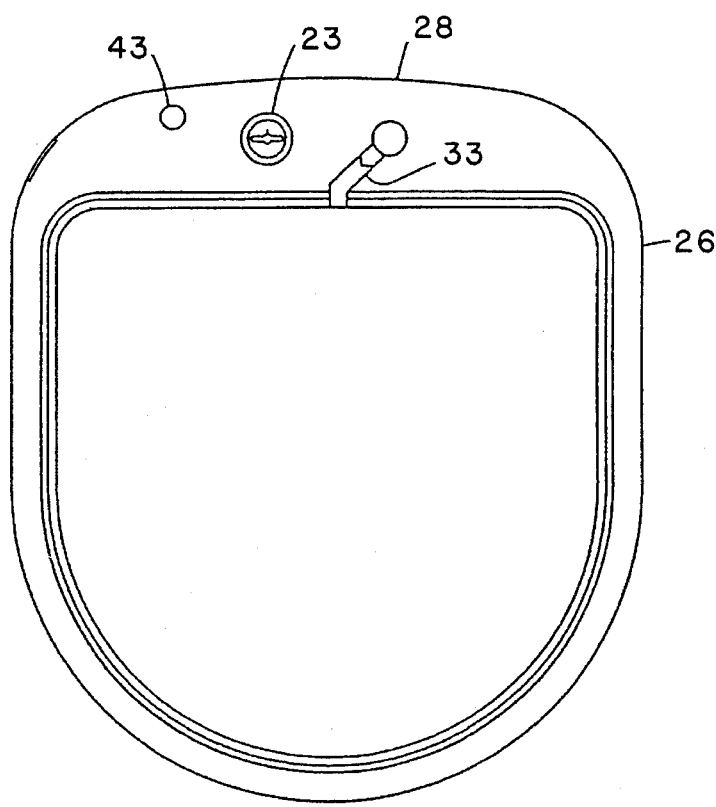
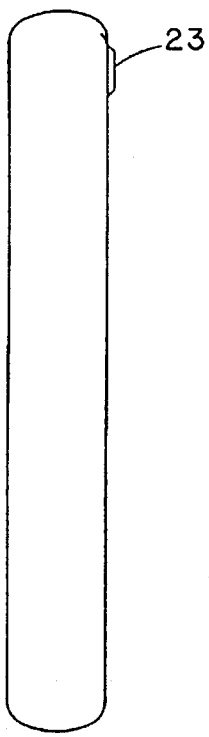
FIG.6C
FIG.6D

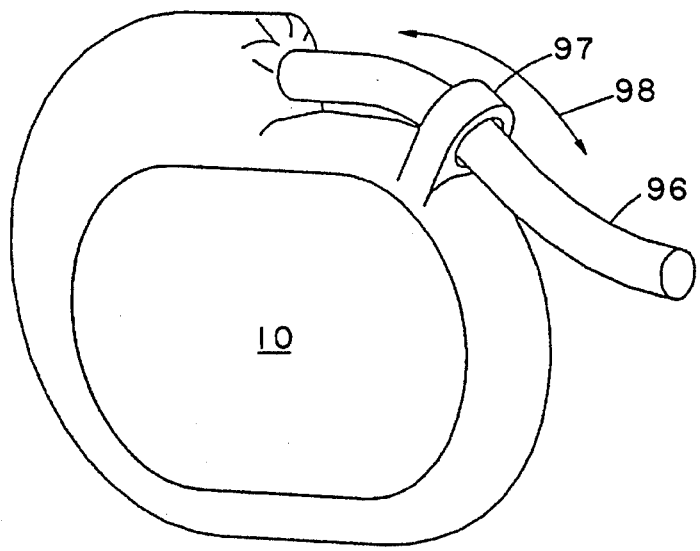
FIG. 10
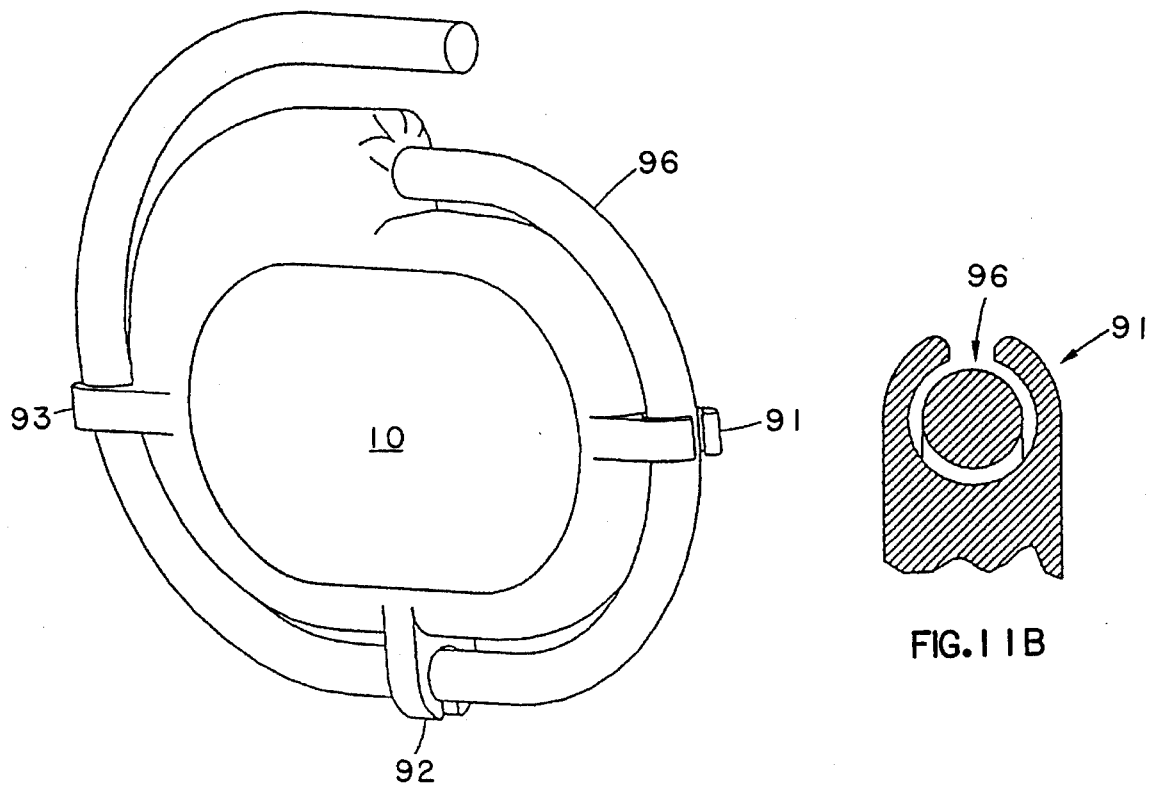
FIG. 11A
FIG. 11B

PACEMAKER

This is a continuation of application(s) Ser. No. 07/766,602 filed on Sep. 26, 1991 now abandoned.

BACKGROUND OF THE INVENTION

1. Field of the Invention

The present invention relates to implantable medical devices and more particularly to an enclosure structure which may be used for implantable medical devices such as: heart pacemakers, pacer/cardioverter/defibrillator and drug administration devices.

2. Description of the Prior Art

The earliest pacemakers typified by U.S. Pat. No. 3,053,356 to Wilson Greatbatch were manufactured of discrete electronic components which were potted in an epoxy resin material and then coated with silicone rubber. Epoxy is permeable to gases and permits battery gases to escape and moisture to enter the device. While operating in the human body such structures became completely perfused with water vapor and reliable operation required that no inorganic salts be present within the device, otherwise electrical short circuits could occur. The Medtronic model 5850 pacemaker is an example of this form of construction.

Continued progress in the development of heart pacemakers resulted in packaging concepts in which the electronic circuitry portion of the pacemaker was enclosed in a hermetically sealed container which was attached to external batteries. The batteries and hermetically sealed package would be potted in epoxy to form the pacemaker. This packaging strategy permitted the mercury-zinc cells to vent their gas while retaining the sensitive electronic components in a hermetic environment which excluded moisture. The Medtronic Xytron pacer is an example of this form of construction.

Development of the solid state lithium iodide battery permitted the inclusion of the electrochemical cell within a hermetic structure. A typical form of modern pacemaker construction is depicted in U.S. Pat. No. 4,314,562 where a hermetically sealed battery is included within a hermetically sealed pacemaker enclosure.

The pacemaker enclosure itself is formed by can halves, which form a "clam shell" assembly. The can halves are welded together along the seam to form the pacemaker pulse generator. Electrical communication to the stimulating leads is done through a plastic connector module fixed to the outer surface of the can and a collection of "feedthroughs" which permit electrical communication with the container but which retain hermeticity of the pacer.

A number of variations on this packaging strategy are known in the art as well. And although conventional construction techniques set forth above have produced reliable long lived pacemakers capable of outlasting their recipients there is a continuing need to improve enclosures for use in pacemakers as well as other implantable medical devices. For example, current construction techniques involve complex assembly operations which increase costs. Current construction techniques require the application of insulating anti-stimulation coatings on the exterior surface of the pacemaker to prevent muscle stimulation. Current construction practices also limit design freedom and do not readily accommodate lead wrap in the pacemaker pocket.

Other problems presented by prior art structures include: the inclusion of weld rings to permit protection of the internal components during butt welding operations; the requirement of cosmetic buffing operations to improve the appearance and biocompatibility of the enclosure; the orientation of, and the number of, feedthroughs required to provide external connections to the implanted device. Many of these features also lead to complex assembly requirements which increases costs and lowers yield from the manufacturing process.

SUMMARY OF THE INVENTION

In contrast to prior art structures, the present invention forms an enclosure from a substantially planar lid which is welded to a circumferential flange formed on a deep drawn shield. The shield and lid form a "container" which is encased in a compliant shroud which isolates the welded flange from direct body contact and which enhances the biocompatibility of the entire device.

The resilient and compliant shroud material accepts connector module components, integrates seals, provides storage for lead wrap, and provides a simple low cost and reliable method of attaching stimulating leads or other structures required by the medical device.

It is preferred that the shield contain a polymeric cup for physically locating and restraining both a battery and a hybrid electronic module.

It is preferred that the electronic module itself be potted with a polymer resin and include reed switch, antenna and other ancillary passive components in an electrically completed subunit. In alternate embodiments the antenna may be locate outside of the container, buried in the shroud to facilitate RF communication with the medical device.

BRIEF DESCRIPTION OF THE DRAWINGS

In the various figures of the drawings, like reference numerals indicate common structure throughout the several views, however it is important to note that three different versions of the structure are shown. More specifically:

FIG. 5A is a side cross section view of the upper insulator spacer;

FIG. 5B is a top cross section view of the upper insulator spacer, with dimension compensation bumps;

FIG. 5C is a detail view of the conformal, contour alignment lip of the top insulator spacer;

FIG. 5D is a front view of the top spacer;

FIG. 5E is a front view of the lower spacer;

FIG. 5F is a side view of the lower spacer;

FIG. 6A is a rear view of the shroud;

FIG. 6B is a side view of the shroud;

FIG. 6C is a front view of the shroud;

FIG. 6D is a side view of the shroud;

FIG. 10 is a perspective view of the device where a lead retention loop is included in the shroud;

FIG. 11A is a perspective view of the device where "split" lead retention loops are included in the shroud;

FIG. 11B is a cross section of a lead retainer loop;

DETAILED DESCRIPTION OF THE ILLUSTRATIVE EMBODIMENT

In the following description, reference is made to several illustrative embodiments of the invention. It should be understood that other embodiments or variations on these embodiments may be utilized without departing from the scope of the invention.

In general, manufacturers of pacers offer pacers in a variety of connector module configurations to facilitate change over of pacemakers onto different styles of chronic leads. The particular shroud structures of the present invention can be adapted to variety of lead standards, with three of the more significant lead standards depicted as specific embodiments.

Each pacer construction embodiment includes a "container" encased in a complimentary "shroud". The shroud configures the pacer to accept the proximal end of a pacemaker lead. Certain structures are common to all embodiments and certain elements are unique to each of the separate embodiments.

Figure 1:
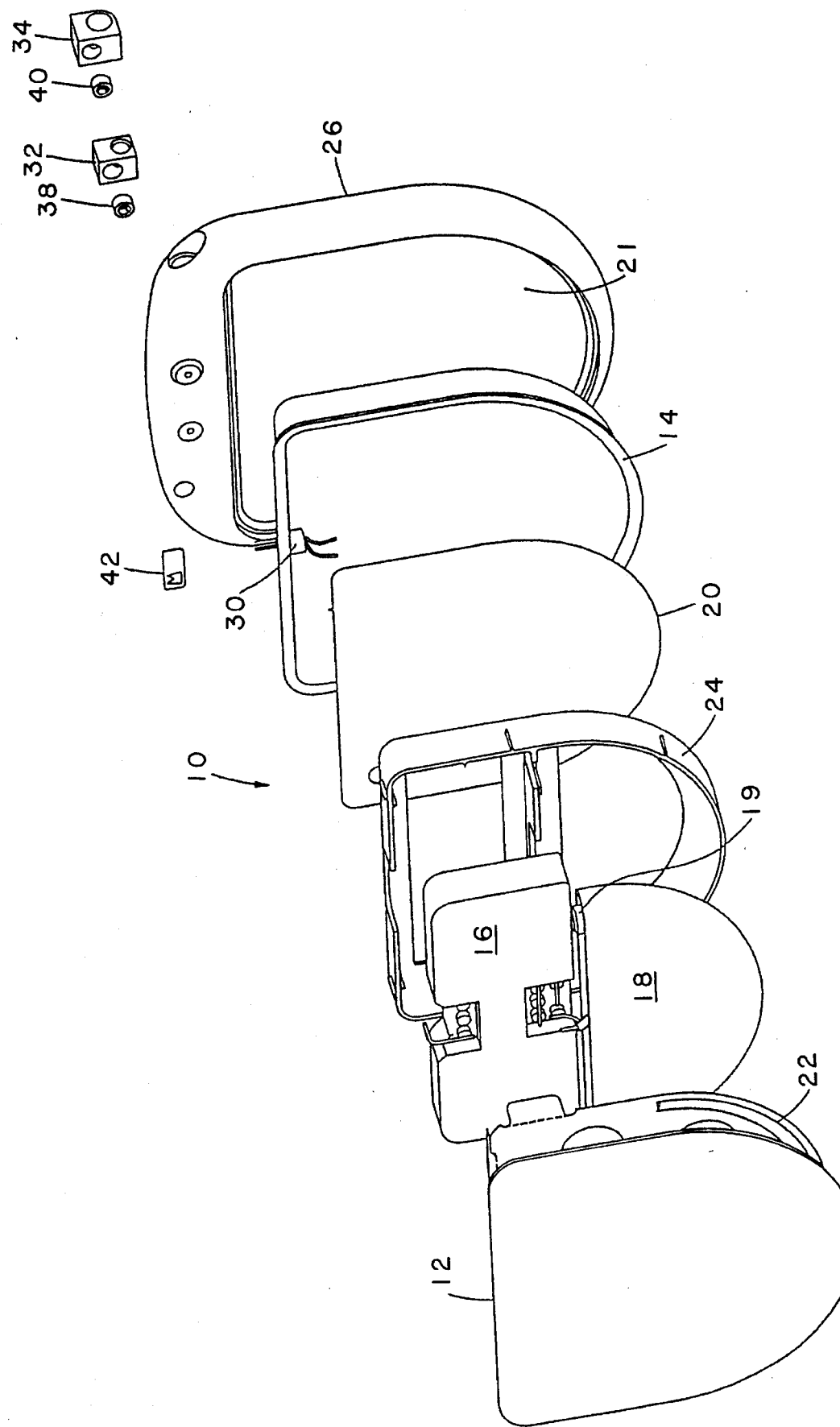
FIG. 1 is an exploded perspective view of the device.
Figure 7:
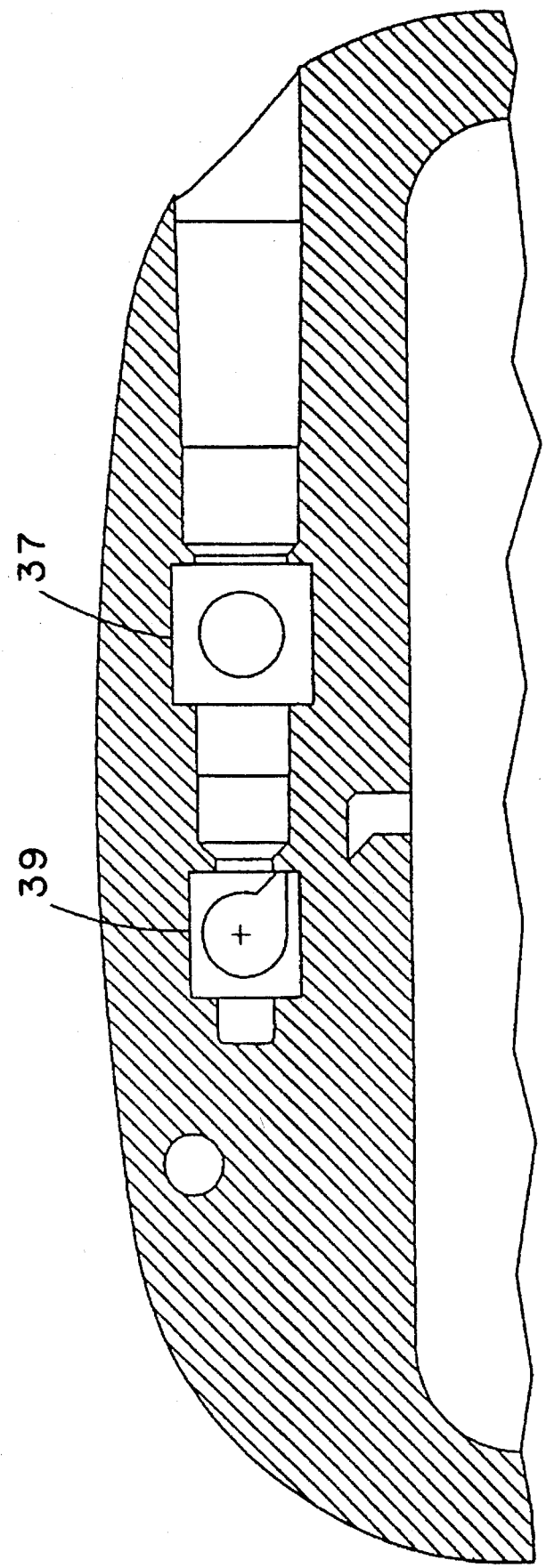
FIG. 7 is a cross section of an IS-1 embodiment of the connector module area.

More particularly, FIGS. 1 and 8 depict a construction suitable for use with a so called "3.2 mm lead"; FIGS. 2, 6, and 7 depict a construction suitable for use with a so called "IS-1 lead"; and FIG. 9 depicts a construction suitable for use with a "unipolar lead". FIGS. 10 through 13 depict lead retention structures and lead support structures which are essentially independent of current industry lead standards. FIGS. 3, 4, and 5 relate to the container structure and are representative of all containers regardless of lead standard.

PART A: GENERAL DESCRIPTION OF PACER CONSTRUCTION

FIG. 1 shows an illustrative and exemplary pacer construction. In this drawing, the major components of the pacer 10 are depicted in an exploded configuration. Although each of the specific embodiments differ in detail, certain aspects of assembly are common to all embodiments. In this regard the exploded device of FIG. 1 is related to a specific embodiment, but is representative of the basic "container" with "shroud" packaging concept.

Turning to FIG. 1, the assembly process encloses several elements in a container formed by the lid 12 and the shield 14. During assembly the lid is sealingly attached to the shield, such as by a welding procedure using a laser, resistance, TIG, brazing, compression or other welding techniques, as well as crimping and such other methods as will result in the formation of a substantially hermetic container. The completed container is identified as 36, for example, in FIG. 2B.

This hermetic container encloses and protects the electronic module 16 and the battery 18, while the container itself, is encased and protected by the shroud 26.

Within the container 36, the electronic module 16 and battery cell 18 are electrically isolated, mechanically protected and positioned by a lower insulator 20, an upper insulator 22 and an insulator cup 24.

Other structures shown in FIG. 1 include the interconnection blocks 32 and 34, and set screw structures, 38 and 40. These elements are located within the connector module of the shroud above the container.

Another structure shown in FIG. 1 is a radiopaque ID 42 which is embedded in the shroud and which permits an identification of the manufacturer and pacing model from an X-ray of the device. Placement of the ID tag in the shroud permits a reduction in its size since the shroud material is less opaque to X-rays.

In summary, the container is sealed and inserted into the shroud 26 along with additional interconnection components. The composite assembly forms the completed pacemaker pulse generator.

Next, the container lid and shield will be described.

Figure 3A:
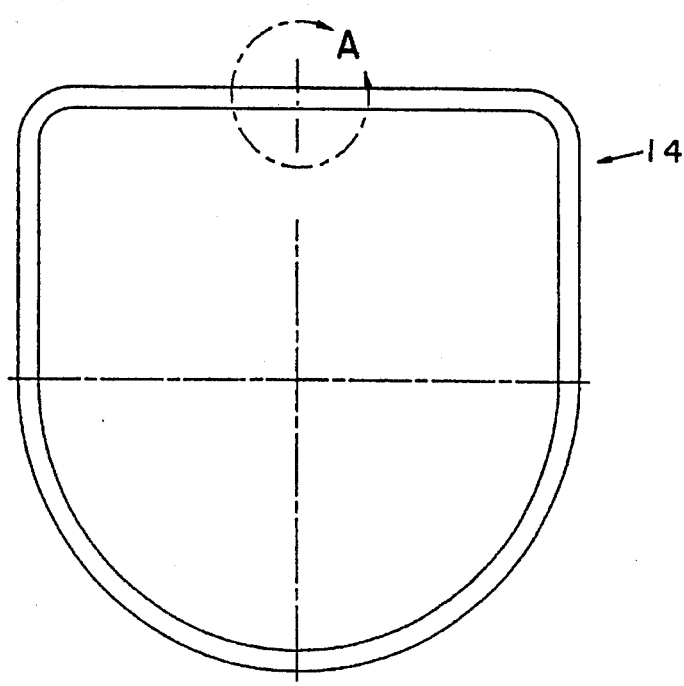
FIG. 3A is a front view of the shield.

FIG. 3A depicts the deep drawn shield 14. This component is stamped or drawn from a sheet of titanium or other suitable material.

Figure 3B:
FIG. 3B is a detail of the flange lip of the shield.

FIG. 3B depicts the flange area. This circumferential flange or lip is provided to facilitate and enhance welding. Traditional clam shell can halves require very tight tolerances to accurate mate the edges for a butt weld. Also, irregular non-planar weld contours are required to accommodate the feedthroughs. Additionally, a weld protection ring is traditionally supplied inside the "clam" to shield the internal components from heat generated during the welding operation. The high tolerance clam shell halves and additional structures, and irregular non-planar weld contours are eliminated with the present design, which can tolerate slight misalignment of the lid 12 and shield 14, during welding.

Figures 3C, 3G:
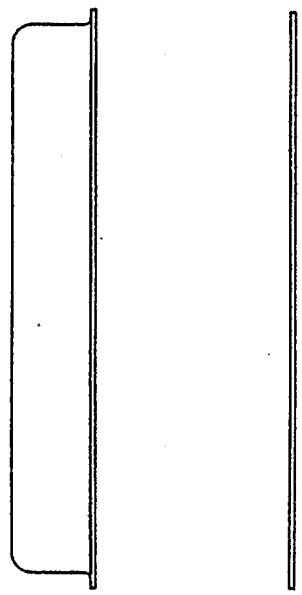
FIG. 3C is a side view of the shield of FIG. 3A.
FIG. 3G is side view of the lid.

FIG. 3C shows the deep drawn contour of the shield. The drawing process disturbs the surface of the sheet stock, however, since these surfaces are not in body contact they may be left in the "as drawn" condition. This reduces the requirement of cosmetic buffing.

Figure 3D:
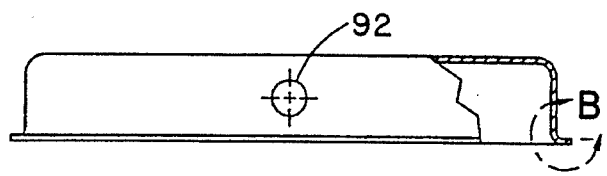
FIG. 3D is a top view of the shield of FIG. 3A.

FIG. 3D shows the top edge of the shield depicting the location of the feedthrough hole 92. For a given pacer thickness the diameter of this hole may be larger than is permitted by clam shell designs.

Figure 3E:
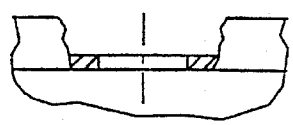
FIG. 3E is a detail of the feedthrough aperture.

FIG. 3E shows the feedthrough aperture in cross section. These two figures illustrate the incorporation of the feedthrough aperture in a continuous surface. In prior art constructions the feedthrough aperture would typically lie very close to or along a seam of the clam shell which presented difficulties in attaching the feedthrough to the can. The location of the feedthrough aperture in an otherwise smooth and continuous surface facilitates the welding operation. An additional benefit is that the thermal stress on the feedthrough is reduced by moving it farther away. Also, the design allows for larger or multiconductor feedthroughs.

Figure 3F:
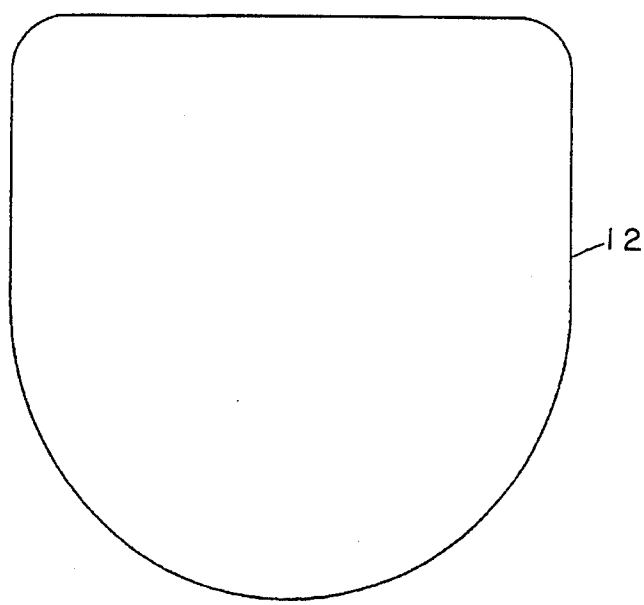
FIG. 3F is top or bottom view of the lid.

FIGS. 3F and 3G show the substantially flat metallic lid 12 which is welded to the shield 14 forming the hermetic container enclosure.

Next, the interior "locating" components of the container will be described.

FIG. 4 depicts the insulator cup 24 in isolation. It is preferred to have uniform wall thickness throughout the cup as shown through the several views in the figures. This structure positions, locates and retains the battery 18 and the electronic module 16. The cup is preferably partitioned into a battery cavity 58 and an electronics module cavity 60. An intermediate web 62 separates the two cavities 60, and 58. This web has a "cutaway" which permits electrical interconnection structures to pass between the two cavities. In the illustrative embodiment the cutaway 64 shown in FIG. 4A permits access to the battery poles. Another cutaway 66 in the web 62 prevents mechanical interference with the battery 18 fill port.

Figure 4A:
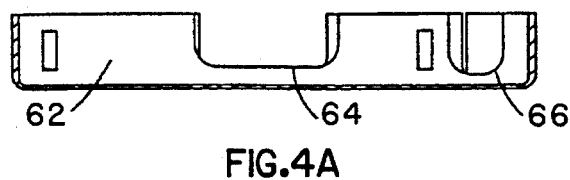
FIG. 4A is a bottom view of the intermediate web of the insulator cup.
Figure 4E:
FIG. 4E is a detail of the module locator nubs of the insulator cup.
Figure 4B:
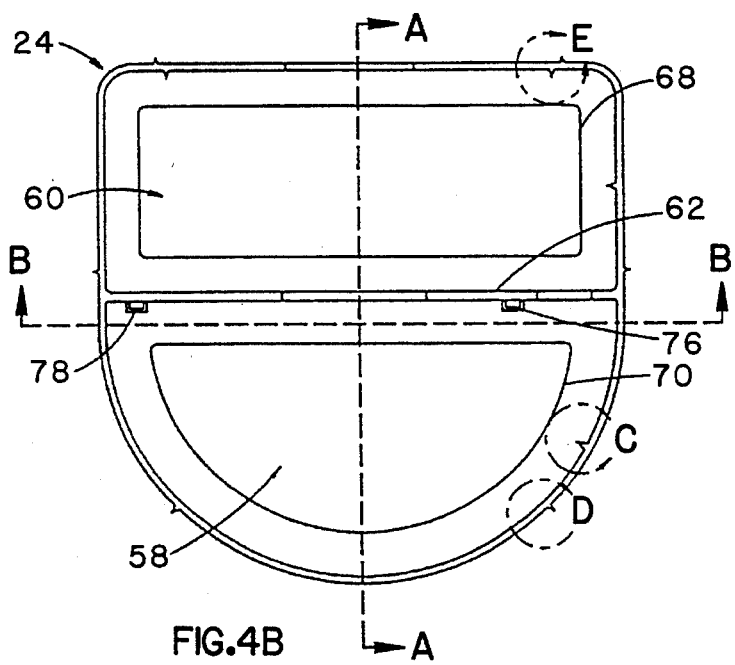
FIG. 4B is a front view of the insulator cup.
Figure 4F:
FIG. 4F is a detail of the battery locator nubs of the insulator cup.
Figure 4C:
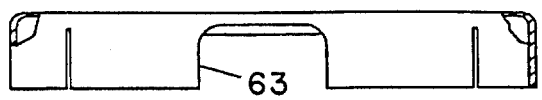
FIG. 4C is a top view of the insulator cup.

As seen in FIG. 4B, the floor of the cup has cutouts 68 and 70. These cutouts as well as the thin and uniform thickness of the cup reduces the amount of water absorptive material within the enclosure and allows room for battery 18 expansion during discharge. In FIG. 4C there is shown a cutaway 63 for permitting coupling between the electronic module 16 and the feedthrough 30.

FIG. 4E shows an illustrative module cavity nub 72 which will deform slightly, forcing and repeatably locating the electronic module against the web 62. In a similar fashion a battery cavity nub, which is identified as 74, and shown in FIG. 4F, forces the battery against the web 62.

Figure 4G:
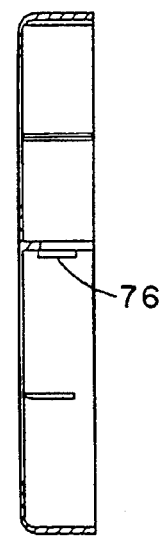
FIG. 4G is a side view section of the insulator cup.
Figure 4D:
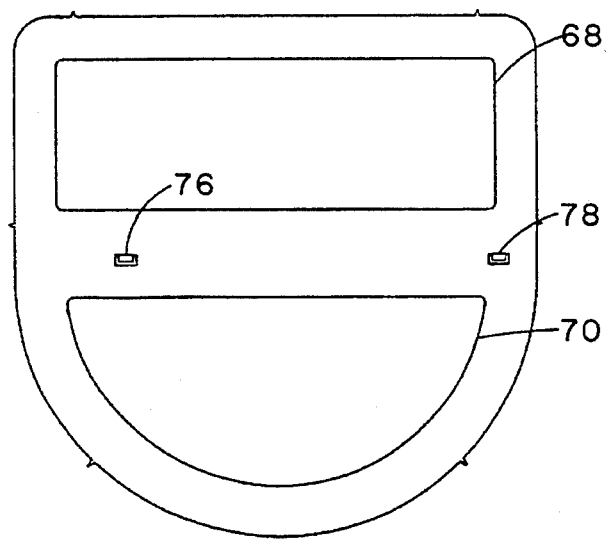
FIG. 4D is a rear view of the insulator cup.
Figure 4H:
FIG. 4H is a detail of the shield locator nubs of the insulator cup.

In a similar fashion, an insulator cup locator nub 99 shown in FIG. 4H deforms slightly upon insertion, forcibly retaining the insulator cup in the shield.

In FIG. 4G, the battery spacer lugs, one of which is shown as 76, permit one of two different sized batteries to be used in the pacer. The small square-form holes adjacent the retainer lugs are present as an artifact of the molding process which generates the rear surface of each lug, as best seen in connection with FIG. 4G and 4D.

The subparts of FIG. 5 show several views of the upper insulator spacer 22, and lower spacer 20. This structure is generally planar and is provided to electrically isolate the module and battery 18 from the metal lid 12 and shield 14, absorb tolerances and act as a shock absorber.

FIG. 5A is a side view which shows the extension of the hemispheric dimples 80, 81, 82, 83, and 84. These dimple structures deform to create a force fit between the inner surface of the lid and the interior of the container. The conformal lip is shown in detail in FIG. 5C. The curved surface reflects the battery contour at the points of contact. This partially circumferential lip 85 as seen in FIG. 5B, helps to stabilize the battery against shock and positions the spacer 22 within the container. The spacer 22 is additionally retained by flaps 100, 101, and 102. The flaps are forcibly retained between the insulator cup and shield 14. FIG. 5D shows that the dimples differ in radius depending upon position on the spacer. In general, the dimples press upon the module or battery at locations where there are no reliefs for welds. FIG. 5E and 5F depict the lower shield insulator 20. This structure is planar and cut to conform to the outline of the bottom of the shield. The hole 88 is provided for clearance and permits evacuation and drying of the interior of the container 34 during manufacture.

Electrical connection between the container and the pacing lead connector block portion 28 of the shroud 26 is performed by a feedthrough 30 as shown in FIG. 1. Interconnection between the feedthrough 30 and the pacing lead is performed by appropriate interconnection blocks within the connector module.

PART B: DESCRIPTION OF THE 3.2 MM EMBODIMENT

FIG. 1 and FIG. 8 depict a pacemaker construction for use with a "3.2 mm standard" lead. This type of lead has concentric, stepped electrode connection areas and a relatively low overall diameter. The 3.2 mm lead differs from an IS-1 lead in that it has no lead seals; these seals are part of the connector module.

As shown in FIG. 1, the shroud 26 has a cavity 21 to accept and retain the container. The shroud is preferably made of a soft conformal rubber material, with urethane and silastic being preferred.

The connector module portion of the shroud retains and positions interconnection blocks 32 and 34. In general these blocks have intersecting passages which accept the lead and set screws 38 and 40. The set screws are tightened by the implanting physician to electrically couple and the fix lead to the pacer 10.

Figure 8A:
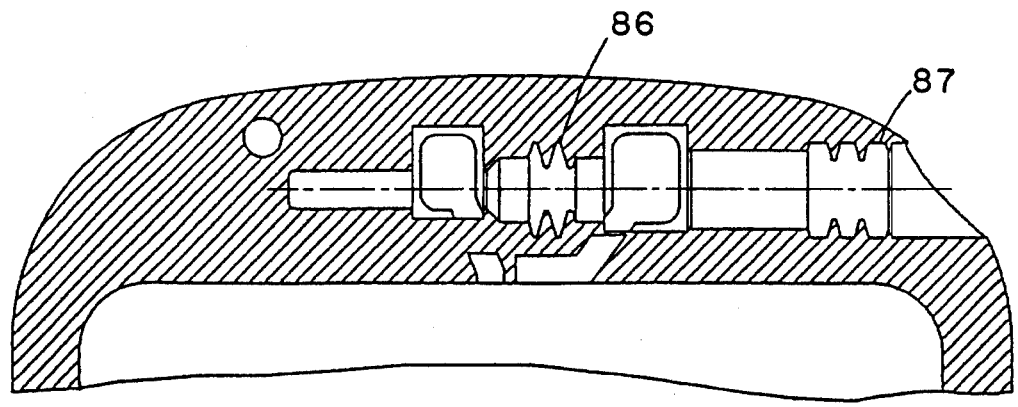
FIG. 8A is a cross section of a small diameter bipolar embodiment of the connector module area.
Figure 8B:
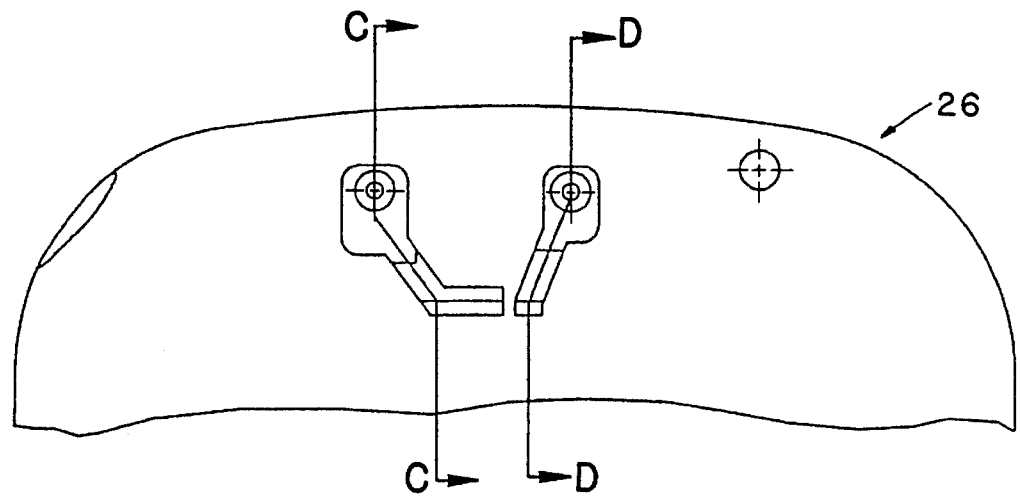
FIG. 8B is a rear view of a small diameter bipolar embodiment of the connector module area.
Figure 8C:
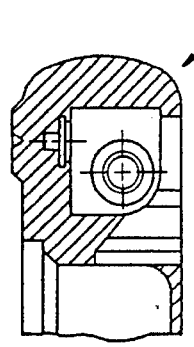
FIG. 8C is a cross section of one of the interconnection module areas of the connector module area depicted in FIG. 8A.
Figure 8D:
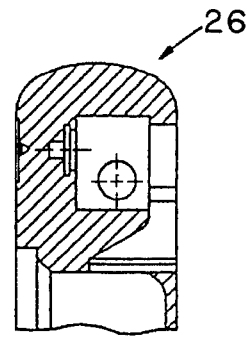
FIG. 8D is a cross section of one of the interconnection module areas of the connector module area depicted in FIG. 8A.

FIG. 8A is a cross section of a connector module area which can accommodate the very small diameter 3.2 mm lead. As shown in the figure, sealing rings 86 and 87 are integrally molded into the connector module to accommodate the stepped lead shank diameters associated with a coaxial lead body.

PART C: DESCRIPTION OF THE IS-1 EMBODIMENT

Figure 2A:
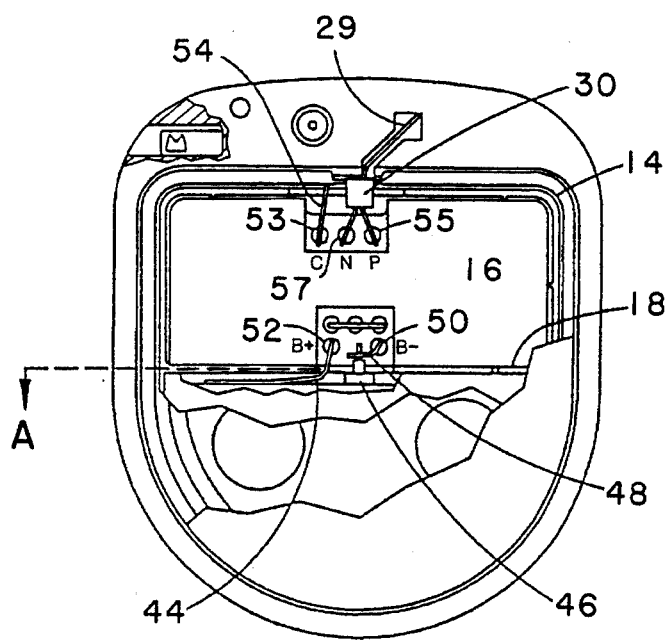
FIG. 2A is a phantom front view of an assembled device.

FIG. 2A shows the invention in the context of an IS-1 lead standard, in phantom section. The electronic module 16 is connected to the battery 18. The positive pole of the battery is the battery case which has a wire 44 welded to it. The negative pole of the battery is formed by a feedthrough 46 located in the battery case. The battery feedthrough wire 48 is welded to a B- power supply connection pin 50 on the module 16. In a similar fashion, one end of the positive pole wire 44 is welded to the battery 16 and the other end to connection pin 52 on the module 16.

Structurally the module 16 is a three terminal device with C,P and N connections. The C connection pin 53 is electrically connected to the shield 14 by welding wire 54 to the shield. The P connection pin 55 and the N connection pin 57 are connected by welding the separate wires of the feedthrough 30 to the N and P connection pins 55 and 57 of the module.

When the intra shield connections are made the completed container may be used as a programmable unipolar/bipolar pacemaker. In the unipolar configuration, one terminal may be the case in the instance of a unipolar pacer, and one of the pacer feedthrough wires 31 may be into the interconnection block aperture formed in the shroud 26. In the bipolar configuration, pacer feedthrough wires 29 and 31 may be into the interconnection block apertures formed in the shroud 26.

Figure 2B:
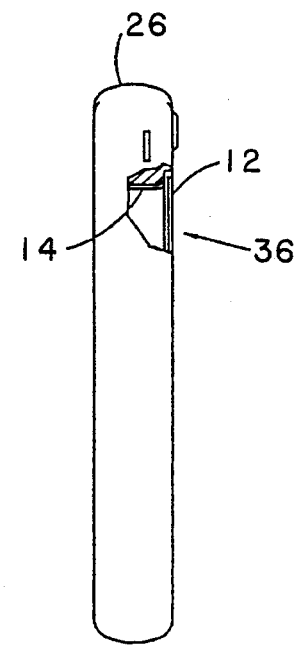
FIG. 2B is a side view of the assembly of FIG. 2A.

FIG. 2B depicts the completed assembly in partial phantom view. The shroud 26 completely surrounds the shield 14. The only metallic surface exposed to the body of the patient is the front surface of the lid 12. In use this lid surface may form the indifferent electrode of a unipolar pacing lead system. Additionally, graphics, including model number, serial number and manufacturing location, are typically engraved on lid 12. Other uses for this surface in an implantable medical device are readily apparent to those skilled in this art.

Figure 2C:
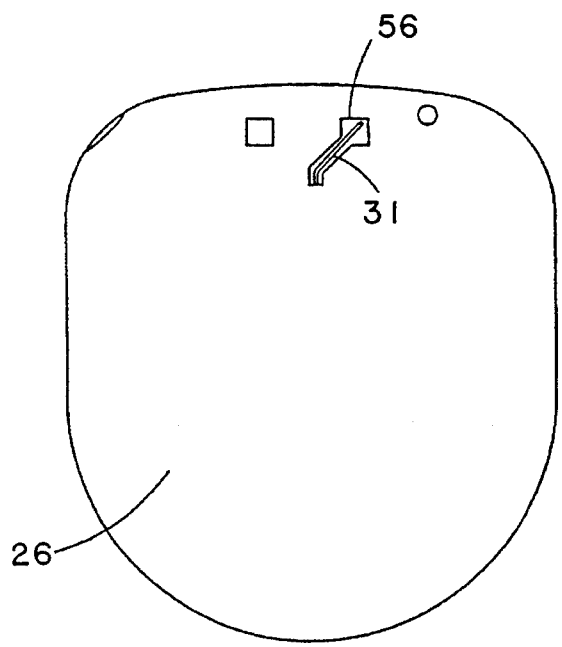
FIG. 2C is a rear view of the assembly of FIG. 2A.

FIG. 2C shows the rear surface of the assembly. The interconnector block aperture 56 permits access to the feedthrough wire 31 for welding purposes. In general, these apertures and other recesses will be backfilled with silastic or other suitable material to prepare the device for use.

Figure 2D:
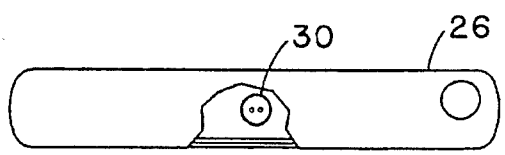
FIG. 2D is a partial phantom top view of the assembly of FIG. 2A.

FIG. 2D shows the position of the feedthrough 30 in the completed device depicted in FIG. 2A. In this particular illustrative embodiment the feedthrough 30 has two wires 31 and 29 passing through the insulator portion of the feedthrough.

Figure 2E:
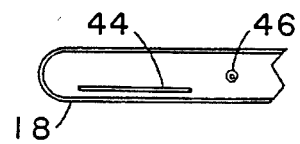
FIG. 2E is a partial top view of the battery portion of the assembly shown in FIG. 2A.

FIG. 2E shows the top surface of the battery 18 as seen in section A—A of FIG. 2A. The hermetically sealed battery can has one pole wire 44 welded to the can top. The other pole is passed through the single lead feedthrough 46.

The IS-1 shroud is shown in the FIG. 6 drawing. In general, the shroud 26 is a molded piece of urethane or silastic and its external contours are shaped to minimize tissue necrosis at the implant site. The resilience of the material and its inertness aid in achieving this objective. The particular shroud depicted in FIG. 6 is adapted to accept a international standard lead referred to in the industry as IS-1. The lead enters the connector module portion 28 of the shroud 26 through the lead acceptance aperture 27 as shown in FIG. 6B. This bipolar IS-1 connector module 28 has one self-sealing integrated grommet 23 to permit access to the set screw 38 used to retain the lead in the connector. The preferred sealing technique is the formation of a slit across the sealing set screw grommet. A second lead to connector contact is made by a sliding spring contact 41.

In general, the connector module portion 28 has cavities to accept the interconnection block 32 and spring contact 41 and a wire connection channel is provided to each, as shown by channels 33 and 35, shown on FIGS. 6C and 6A respectively. A suture hole 43 is provided to allow the implanting physician to tie the pacemaker to tissue in the implant pocket to prevent erosion and pacemaker rotation.

FIG. 7 is a detail taken along section D—D of FIG. 6B. The interconnection block cavity 37 and 39 accept the block 32 and spring contact 41. The deformable nature of the shroud material permits insertion of the block and spring contact into the cavities during assembly.

Figure 9A:
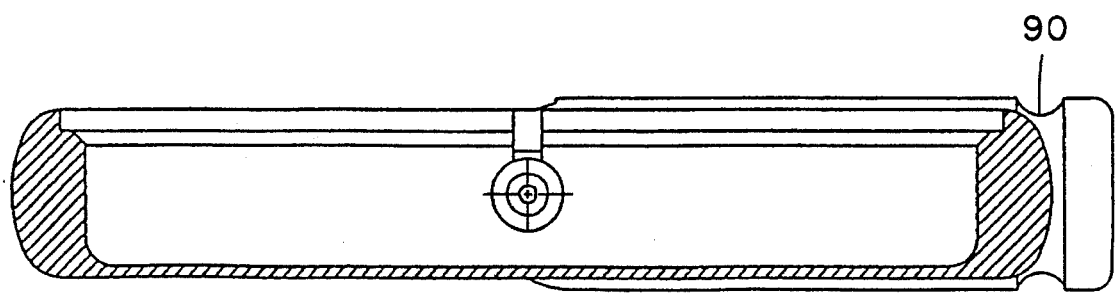
FIG. 9A is a cross section of a unipolar connector module embodiment of the shroud, viewing the area under the connector module.
Figure 9B:
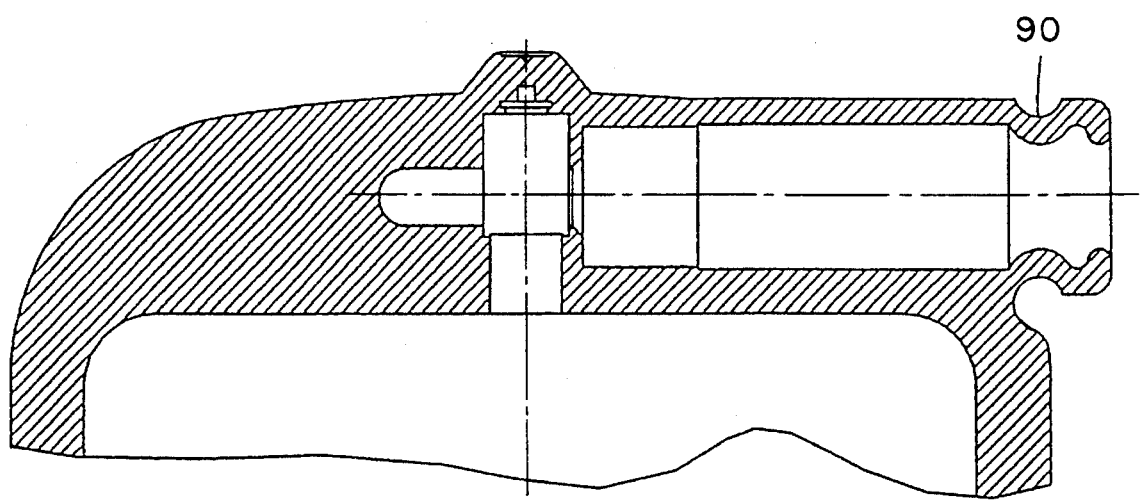
FIG. 9B is a cross section of a unipolar connector module embodiment of the shroud.

A simpler connector module area can be made to accommodate early style unipolar leads as shown in FIG. 9A and FIG. 9B. In this embodiment a suture tie area 90 can be molded into the connector module area.

FIG. 10 shows a modification of the basic structure to include a lead retainer 97. The lead retainer "wraps" the lead body 96 around the pacer along path 98. The arcuate path 98 ensures that tension on the lead 96 is not directly coupled to the connector block area of the shroud. Instead, tension forces deflect the retention loop 97 which grips the lead body 96 and transfer the forces to the periphery of the shroud, at the base of the lead retainer.

FIG. 11A is an alternate form of the lead retention loops which are split, to facilitate lead insertion. An isolated lead retention block is shown in FIG. 11B.

Figure 12A:
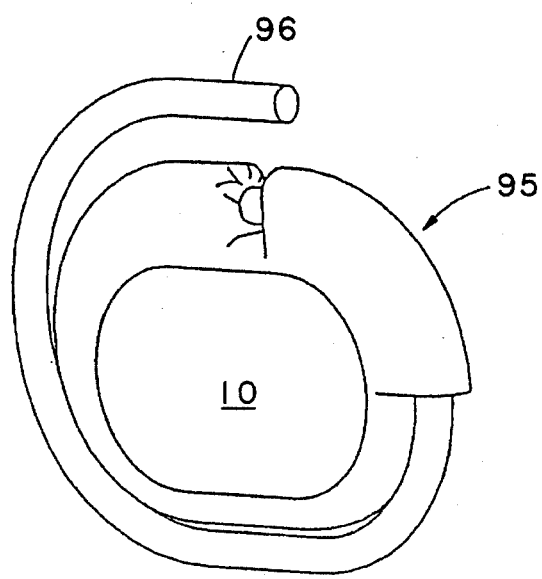
FIG. 12A is a perspective view of the device where the shroud retains the lead in the device.
Figure 12B:
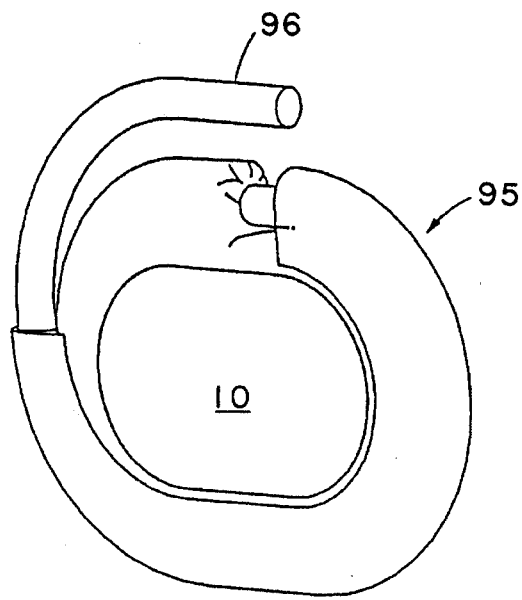
FIG. 12B is a perspective view of the device where the shroud retains the lead in the device.

With either the FIG. 11 or FIG. 12 embodiment, the proximal end of the lead can be retained in the connector module without set screws or other retention features.

FIG. 12 is an alternate form of the shroud system which includes a circumferential hood 95 which retain the lead wrap in the same plane as the pacer. This lead retention feature will also avoid the possiblity of the lead wrap otherwise coming into contact with either face of the pacemaker can and thus interfering with its function. A particular concern of such interfering lead wrap, for example, arises in the context of an activity-based transducer bonded to the face of the pacemaker can, such as Medtronic Model No. 8400 "Activitrax" and corresponding U.S. Pat. No. 4,428,378, to Anderson, incorporated herein by reference. In a pediatric application, this feature permits the excess lead to be stored against the pacer and permits the lead to "unwind" as the patient grows.

Figure 13A:
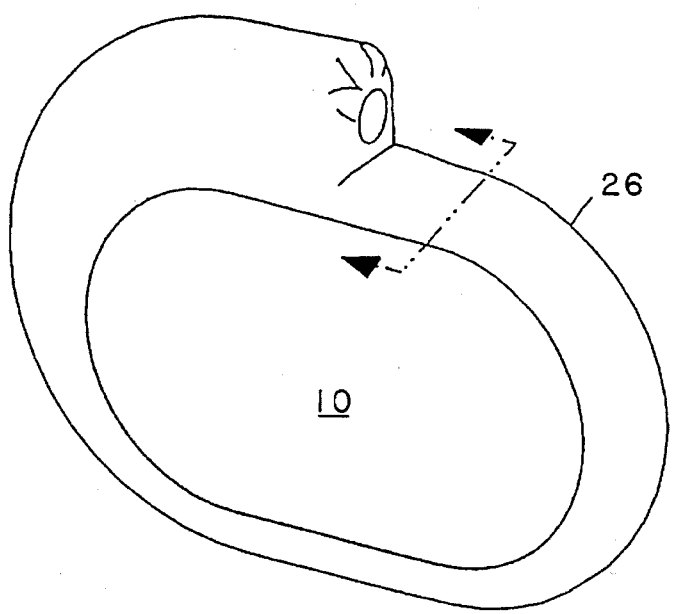
FIG. 13A is a perspective view of the device where the shroud contains a "buried" antenna.
Figure 13B:
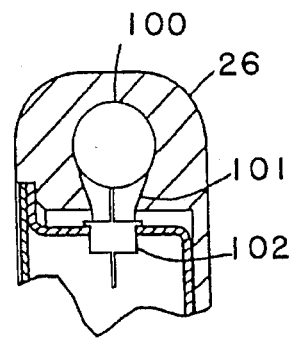
FIG. 13B is a cross section of the buried antenna embodiment.

FIGS. 13A and 13B illustrate an embodiment where the shroud 26 of pacer 10 contains an antenna 100 buried in a cavity 101 in the shroud 26. Locating the antenna in the shroud, for example, will advantageously reduce the power dissipation otherwise associated with telemetric transmissions through the medical device container, typically formed of titanium metal. This will allow reductions in size, increased longevity, improved telemetry performance, and other benefits. In this configuration, a feedthrough 102 is provided to provide electrical communication between the enclosure and the antenna 101.

We claim:

1. An implantable medical device, comprising:
   (A) a substantially hermetic container, comprising:
      (1) a lid having a circumferential lid edge surface;
      (2) a shield having a bottom wall and a circumferential side wall connected to said bottom wall and terminating at an outer circumferential flange surface overlapping and sealingly attached to said circumferential lid edge surface to provide said container;
   (B) an electronic circuit located within said container;
   (C) a feedthrough extending through said shield and coupled to said electronic circuit;
   (D) a shroud of a resilient, compliant plastic having a connector bore means for receiving a connector of an electrical lead formed therein and enclosing said circumferential lid edge surface, said flange surface and said feedthrough; and
   (E) an electrical connector means for coupling to an electrical lead, mounted in said material of said shroud, coupled to said feedthrough and exposed to said connector bore means.

2. An implantable medical device according to claim 1, further comprising insulators located within said container disposed adjacent said lid and said bottom wall of said shield.

3. An implantable medical device according to claim 1, wherein said electronic circuit comprises a pulse generator, coupled to said feedthrough.

4. An implantable medical device according to claim 3, wherein said pulse generator is further coupled to said shield.

5. An implantable medical device according to claim 1, further comprising a power source located in said container and coupled to said electronic circuit.

6. An implantable medical device according to claim 1, further comprising a radio-opaque identifier mounted to said shroud.

7. An implantable medical device according to claim 1, wherein said feedthrough extends through said circumferential side wall.

8. An implantable medical device according to claim 1, wherein said shroud covers said bottom wall of said shield.

9. An implantable medical device according to claim 1, further comprising an insulator cup located in said shield and comprising means for retaining said electronic circuit in a desired location within said device.

10. An implantable medical device according to claim 1, wherein said shroud further comprises means for engaging an electrical lead body.

11. An implantable medical device, comprising:
(A) a substantially hermetic container having a circumferential edge surface;
(B) an electronic circuit located within said container;
(C) a feedthrough extending through said container and coupled to said electronic circuit;
(D) a shroud of a resilient, compliant material having a connector bore means for receiving a connector of an electrical lead formed therein and enclosing said circumferential edge surface and said feedthrough; and
(E) an electrical connector means for coupling to an electrical lead, mounted in said material of said shroud, coupled to said feedthrough and exposed to said connector bore means.

12. An implantable medical device according to claim 11, wherein said container has a generally planar wall surface exposed to the exterior of said shroud.

13. An implantable medical device according to claim 12, wherein said electronic circuit comprises a pulse generator and wherein said pulse generator is coupled to said wall surface and to said feedthrough.

14. An implantable medical device according to claim 11, further comprising a second feedthrough, coupled to said electronic circuit and enclosed by said shroud, and a second electrical connector means coupled to said second feedthrough.

15. An implantable medical device according to claim 14, wherein said electronic circuit comprises a pulse generator and wherein said pulse generator is coupled to said first and second feedthroughs.

16. An implantable medical device, comprising:
(A) a substantially hermetic container having a circumferential edge surface;
(B) an electronic circuit located within said container;
(C) a feedthrough extending through said container and coupled to said electronic circuit;
(D) a shroud fabricated of a resilient material, having a connector bore formed therein and enclosing said circumferential edge surface and said feedthrough; and
(E) an electrical connector means for coupling to an electrical lead, mounted in said shroud, coupled to said feedthrough and exposed to said connector bore, wherein a portion of said resilient material of said shroud is formed to define an integrated sealing grommet adjacent said electrical connector means.

17. An implantable medical device, comprising:
(A) a substantially hermetic container having a circumferential edge surface;
(B) an electronic circuit located within said container;
(C) a feedthrough extending through said container and coupled to said electronic circuit;
(D) a shroud fabricated of a resilient, compliant material, having a connector bore means for receiving an electrical connector of an electrical lead formed therein and enclosing said circumferential edge surface and said feedthrough;
(E) an electrical connector means for coupling to an electrical lead, mounted in said shroud, coupled to said feedthrough and exposed to said connector bore; and
(F) an antenna coupled to said electronic circuit, positioned outside said container and mounted in said material of said shroud.

18. An implantable medical device, comprising:
(A) a metal container sealed against fluid ingress and having opposing, generally planar major surfaces and a circumferential edge surface;
(B) an electronic circuit located within said container;
(C) a shroud fabricated of resilient, compliant material having a connector bore means for receiving an electrical connector of an electrical lead formed therein and enclosing said circumferential side wall; and
(D) an electrical connector mounted in said material of said shroud, coupled to said electronic circuit and exposed to said connector bore means.

19. An implantable medical device, according to claim 18, wherein a portion of said material of said shroud is formed into to an integrated sealing grommet adjacent said electrical connector.

* * * * *